(12) United States Patent
Hwang et al.

(10) Patent No.: US 7,672,702 B2
(45) Date of Patent: Mar. 2, 2010

(54) NONINVASIVE IN VIVO MEASURING SYSTEM AND NONINVASIVE IN VIVO MEASURING METHOD BY CORRECTING INFLUENCE OF HEMOGLOBIN

(75) Inventors: In Duk Hwang, Yongin-si (KR); Jae Chan Park, Yongin-si (KR); Kyung Ho Kim, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 364 days.

(21) Appl. No.: 11/717,210

(22) Filed: Mar. 13, 2007

(65) Prior Publication Data
US 2008/0228050 A1    Sep. 18, 2008

(51) Int. Cl.
*A61B 5/1455* (2006.01)
(52) U.S. Cl. ........................... 600/316; 600/317
(58) Field of Classification Search ............... 600/316, 600/322, 334, 335

See application file for complete search history.

(56) References Cited

U.S. PATENT DOCUMENTS

| | | | |
|---|---|---|---|
| 6,289,230 B1 * | 9/2001 | Chaiken et al. | 600/322 |
| 6,400,972 B1 * | 6/2002 | Fine | 600/322 |
| 2002/0173709 A1 * | 11/2002 | Fine et al. | 600/335 |
| 2003/0225320 A1 * | 12/2003 | Jeon et al. | 600/310 |

* cited by examiner

*Primary Examiner*—Eric F Winakur
*Assistant Examiner*—Etsub D Berhanu (57) ABSTRACT

A noninvasive in vivo measuring system and a noninvasive in vivo measuring method are provided. In the noninvasive in vivo measuring system, a Raman-fluorescence measuring unit measures blood sugar concentration, which is measured using Raman spectra before and after applying a pressure on a finger, and outputs a final blood sugar level by correcting the blood sugar concentration measurement according to a Hemoglobin (Hb) concentration measured by an Hb measuring unit.

18 Claims, 9 Drawing Sheets

NONINVASIVE IN VIVO MEASURING SYSTEM AND NONINVASIVE IN VIVO MEASURING METHOD BY CORRECTING INFLUENCE OF HEMOGLOBIN

BACKGROUND OF THE INVENTION

1. Field of the Invention

The present invention relates to a blood sugar measuring system. More particularly, the present invention relates to a noninvasive in vivo measuring system and a noninvasive in vivo measuring method which can accurately measure blood sugar by correcting influence of Hemoglobin (Hb) concentration.

2. Description of Related Art

Improved lifestyles have increased adult diseases. This also has increased peoples' concerns about their health.

Diabetes is one type of adult disease and the number of diabetics is also significantly rising.

Diabetes is a medical condition in which someone has too much glucose, that is, blood sugar in their blood because of the lack of insulin in their body and discharges the glucose along with the urine. Accordingly, diabetics need to test their blood sugar about six times a day in order to adjust the blood sugar in their blood. Also, blood sugar is one of the most important components informing a person of their state of health. In the case of a normal state, the blood sugar is maintained between 70 and 110 mg/dl (mg per 100 $cm^3$). After meals, the blood sugar is maintained at less than 180 mg/dl. Also, even in the case of an empty stomach, the blood sugar is maintained at more than 60 mg/dl. However, when the blood sugar rises up to more than a normal state, a person may become dehydrated because of frequent urine, etc. When the blood sugar falls below a normal state, a person may have a feeling of uneasiness, vertigo, etc. Also, this may slow brain activities and if it gets more serious, brain cells may be damaged and consequently, a person may fall into a coma or die.

In a conventional blood sugar measuring method, an invasive method, that is a user invasively draws blood from a body and measures blood sugar concentration via blood sugar measuring instrument using an enzymatic method, is frequently used. In the invasive method, the user draws blood, the drawn blood reacts to a diagnostic reagent, and the blood is diagnosed using a clinical analyzer or a color change of a strip, having been reacted to the diagnostic reagent.

However, the conventional invasive blood sugar measuring method may inflict pain upon a diabetic patient due to a procedure of drawing blood, and also the diabetic patient may become infected with another disease due to repeated operations of drawing blood. Also, the conventional invasive blood sugar measuring method has disadvantages, in that constant monitoring is impossible and coping with an emergency situation is not simple since it requires time to draw blood. Also, the diabetic patient may incur many expenses, and waste may occur since a great deal of strips and diagnostic reagents are used, and accordingly, environmental pollution may occur due to the waste in the conventional invasive blood sugar measuring method.

To control blood sugar for the diabetic patient or to medically examine a healthy person, a technique which can measure blood sugar concentration without drawing blood and without the strips and diagnostic reagents is required. Accordingly, a noninvasive blood sugar measuring method enhancing a user's convenience has been developed and used for a limited number of users.

Figure 1:
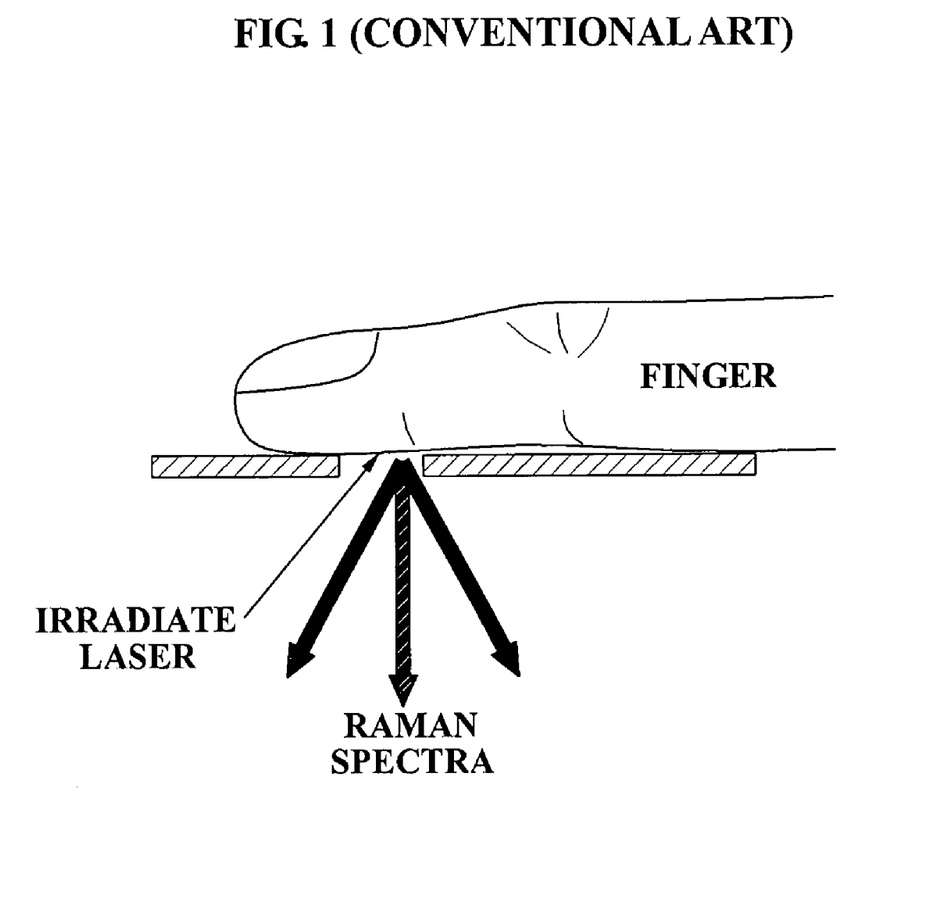
FIG. 1 is a diagram illustrating measuring blood sugar via a general tissue modulation in a conventional art.

As illustrated in FIG. 1, in a blood sugar measuring method via a tissue modulation, one noninvasive blood sugar measuring method, when a laser which is irradiated on a finger is reflected, Raman-fluorescence spectra with respect to the reflected laser analysis is used. A phenomenon in which each component in blood has a unique Raman wavelength, and thus changes spectrum, is used.

In the Raman-fluorescence method, a blood sugar level is measured by analyzing Raman spectra, being scattered in response to a glucose component in blood and occurring in a corresponding wavelength, among fluorescence spectra of the reflected laser. This is disclosed in the U.S. Pat. No. 6,289,230.

Figure 2:
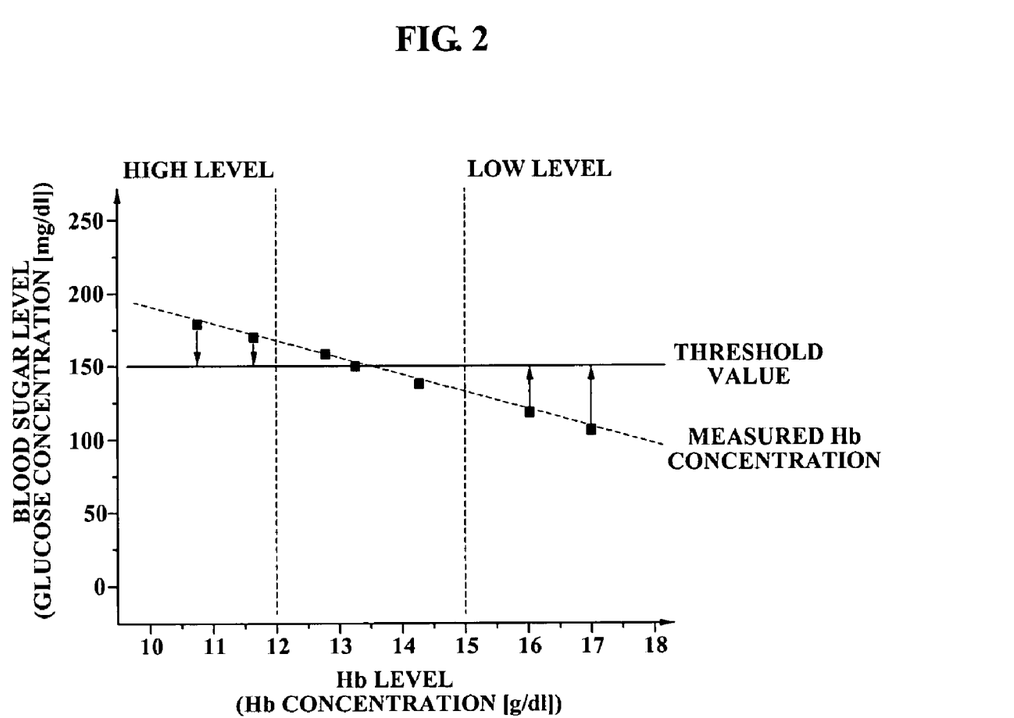
FIG. 2 is a graph illustrating a general relation between an Hb level and a blood sugar level.

However, the blood sugar level may not be regularly measured via the above tissue modulation in the conventional Raman-fluorescence method since the Raman spectra in response to the glucose component are affected by the other components in the blood. Specifically, as illustrated in FIG. 2, the blood sugar level is randomly shown depending on an amount of the Hb in blood.

BRIEF SUMMARY

An aspect of the present invention provides a noninvasive in vivo measuring system and a noninvasive in vivo measuring method which can enhance accuracy when measuring blood sugar by correcting an influence of Hemoglobin (Hb).

An aspect of the present invention also provides a noninvasive in vivo measuring system and a noninvasive in vivo measuring method which can correct a blood sugar measurement, which is measured in a Raman-fluorescence method, by using an Hb concentration.

An aspect of the present invention also provides a noninvasive in vivo measuring system and a noninvasive in vivo measuring method which can reduce an error for each person, occurring due to Hb concentration when measuring blood sugar in a Raman-fluorescence method, and correct a measured blood sugar value using an Hb concentration.

According to an aspect of the present invention, there is provided a noninvasive in vivo measuring system including: a tissue modulation unit applying a pressure on a tissue; an Hb measuring unit analyzing an amount of absorption of electromagnetic waves on a first portion of the tissue before and after the applying of the pressure by the tissue modulation unit, and measuring Hb concentration of the tissue; and a Raman-fluorescence (R-F) measuring unit measuring blood sugar concentration by analyzing Raman spectra based on a reflection of a laser irradiated on a second portion of the tissue before and after the applying of the pressure by the tissue modulation unit, and calculating a final blood sugar level by correcting the blood sugar concentration measurement, having been measured based on the measured Hb concentration. The Hb measuring unit calculates the Hb concentration of the tissue by analyzing absorption of predetermined electromagnetic waves before and after applying the pressure on the tissue and wavelengths of the electromagnetic waves before and after the applying of the pressure are less than approximately 1300 nm.

The R-F measuring unit calculates the final blood sugar level by increasingly correcting the blood sugar concentration measurement, having been measured based on the Raman spectra, when the Hb concentration is greater than a predetermined threshold value, and calculates the final blood sugar level by decreasingly correcting the blood sugar concentration measurement, having been measured based on the Raman spectra, when the Hb concentration is less than the predetermined threshold value.

The tissue modulation unit applies a predetermined pressure between the instrument for contacting the tissue and a portion of the tissue.

According to another aspect of the present invention, there is provided a noninvasive in vivo measuring method including: analyzing an amount of absorption of electromagnetic waves on a first portion of a tissue; analyzing Raman spectra based on a reflection of a laser irradiated on a second portion of the tissue; applying a pressure on the tissue; analyzing the amount of absorption of electromagnetic waves on the first portion of the tissue after the applying of the pressure; analyzing the Raman spectra based on the reflection of the laser irradiated on the second portion of the tissue after the applying of the pressure; measuring Hb concentration of the tissue using a difference of the absorption of the electromagnetic waves on the first portion of the tissue before and after applying the pressure; measuring blood sugar concentration of the tissue using a difference of the Raman spectra on the second portion of the tissue before and after the applying of the pressure; and measuring a final blood sugar level by correcting the blood sugar concentration measurement according to the measured Hb concentration.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF EMBODIMENTS

Reference will now be made in detail to exemplary embodiments of the present invention, examples of which are illustrated in the accompanying drawings, wherein like reference numerals refer to the like elements throughout. The exemplary embodiments are described below in order to explain the present invention by referring to the figures.

Figure 3:
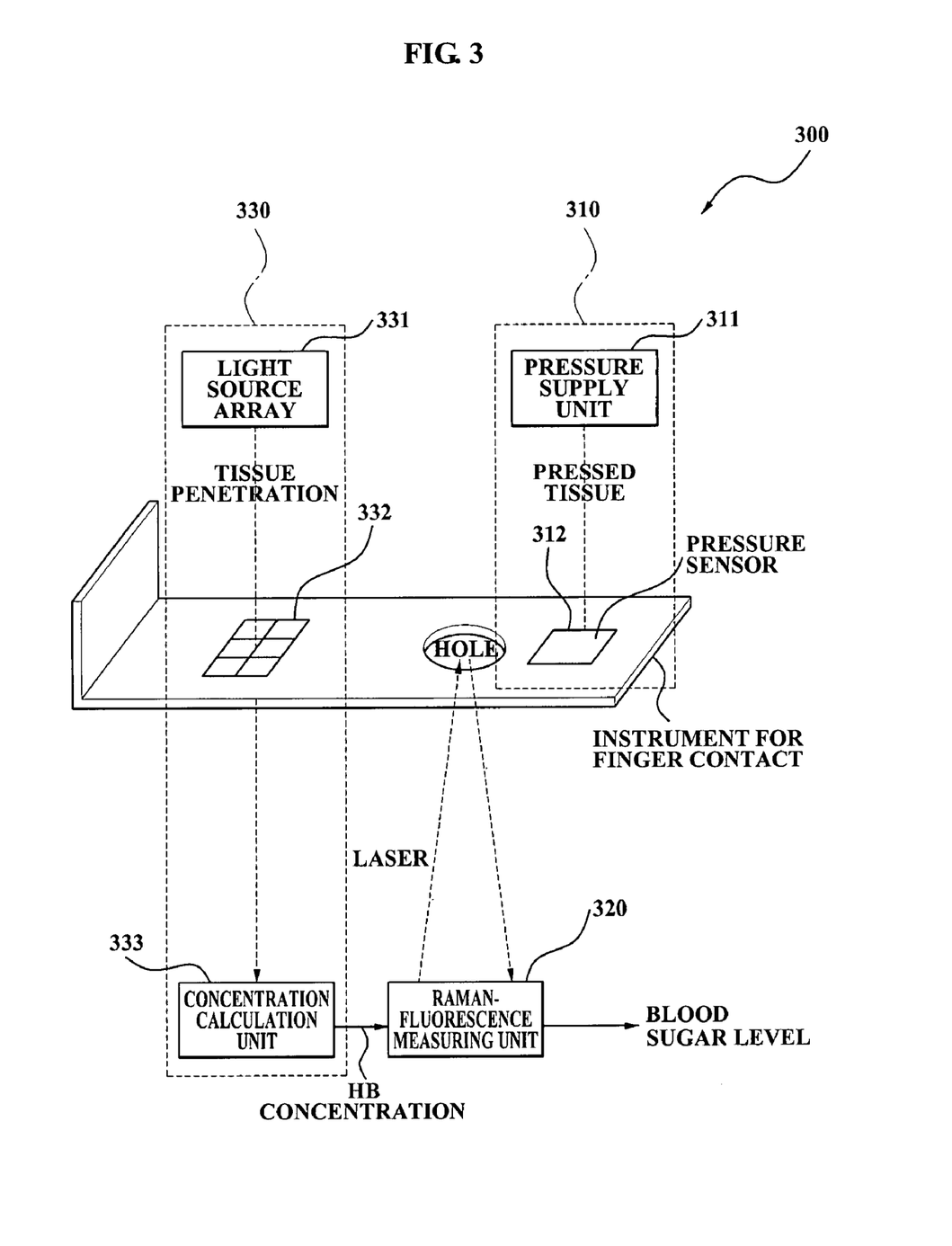
FIG. 3 is a diagram illustrating a noninvasive in vivo measuring system according to an embodiment of the present invention.

FIG. 3 is a diagram illustrating a noninvasive in vivo measuring system 300 according to an embodiment of the present invention. Referring to FIG. 3, the noninvasive in vivo measuring system 300 according to the embodiment of the present invention includes a tissue modulation unit 310, a Raman-fluorescence (RF) measuring unit 320, and a Hemoglobin (Hb) measuring unit 330.

The noninvasive in vivo measuring system 300 according to an embodiment of the present invention noninvasively measures blood sugar with respect to a predetermined portion of a finger (the predetermined portion of the finger is referred to as a 'tissue'), contacted to a predetermined instrument.

The noninvasive in vivo measuring system 300 according to the embodiment of the present invention includes the tissue modulation unit 310 for applying a pressure on the tissue, and the tissue modulation unit 310 includes a pressure apply unit 311 and a pressure sensor 312.

Figure 4:
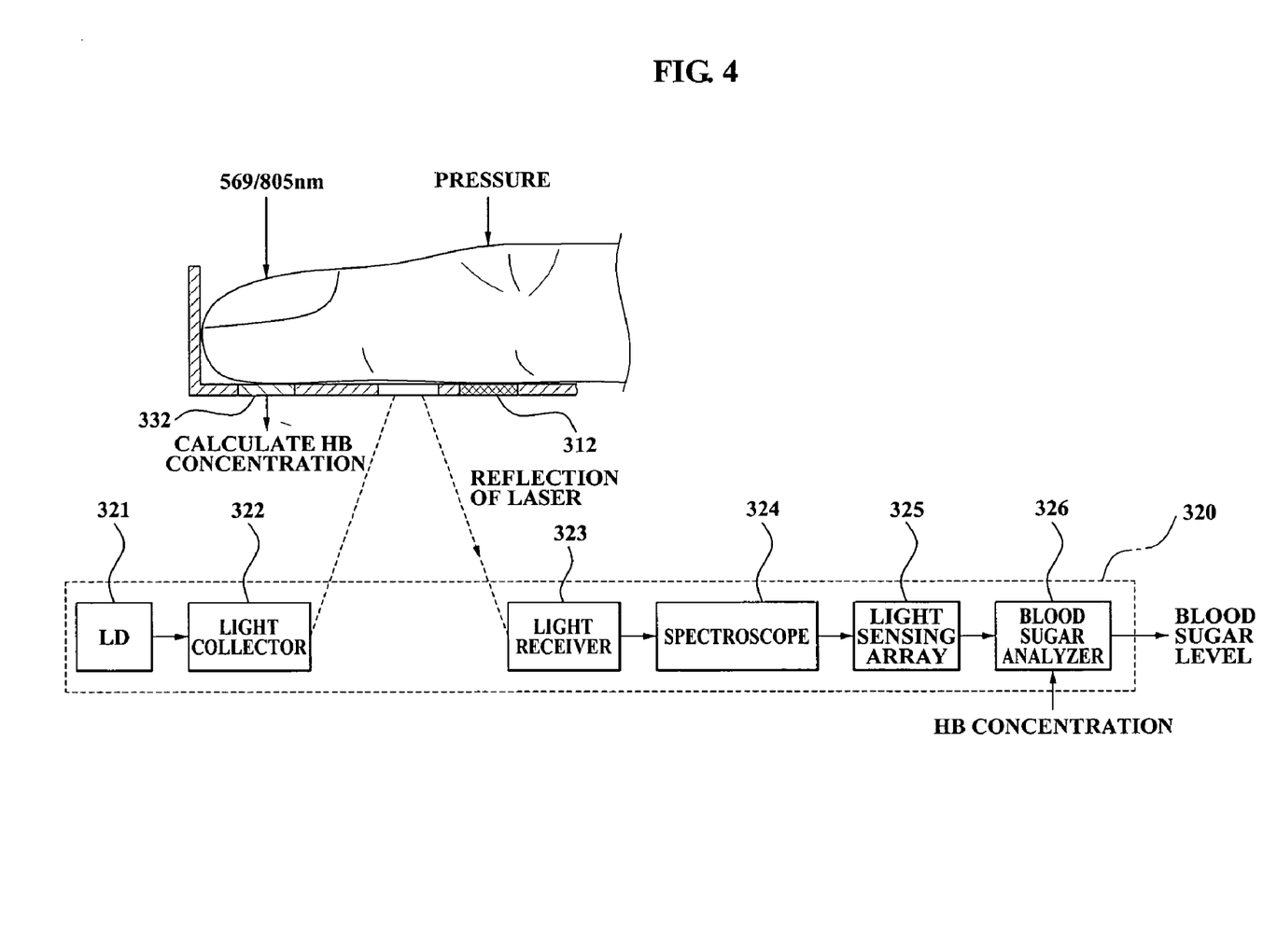
FIG. 4 is a diagram illustrating a Raman-fluorescence measuring unit of FIG. 3.

As illustrated in FIG. 4, the R-F measuring unit 320 includes a laser diode (LD) 321, a light collector 322, a light receiver 323, a spectroscope 324, a light sensing array 325, and a blood sugar analyzer 326.

The R-F measuring unit 320 measures blood sugar concentration by analyzing Raman spectra based on a reflection of a laser irradiated on a predetermined portion of the finger before and after applying a pressure on the tissue.

Specifically, the noninvasive in vivo measuring system 300 according to the embodiment of the present invention includes the Kb measuring unit 330 to measure Kb concentration of the tissue, the Hb measuring unit 330 includes a light source array 331, a light detector 332, and a concentration calculation unit 333. The Hb measuring unit 330 calculates the Hb concentration of the tissue by analyzing absorption of predetermined electromagnetic waves before and after applying the pressure on the tissue.

Accordingly, the R-F measuring unit 320 calculates a final blood sugar level by correcting the blood sugar concentration measurement, which has been measured based on the analysis of the Raman spectra before and after applying the pressure by the R-F measuring unit 320, according to the Hb concentration having been measured by the Hb measuring unit 330.

Figure 5:
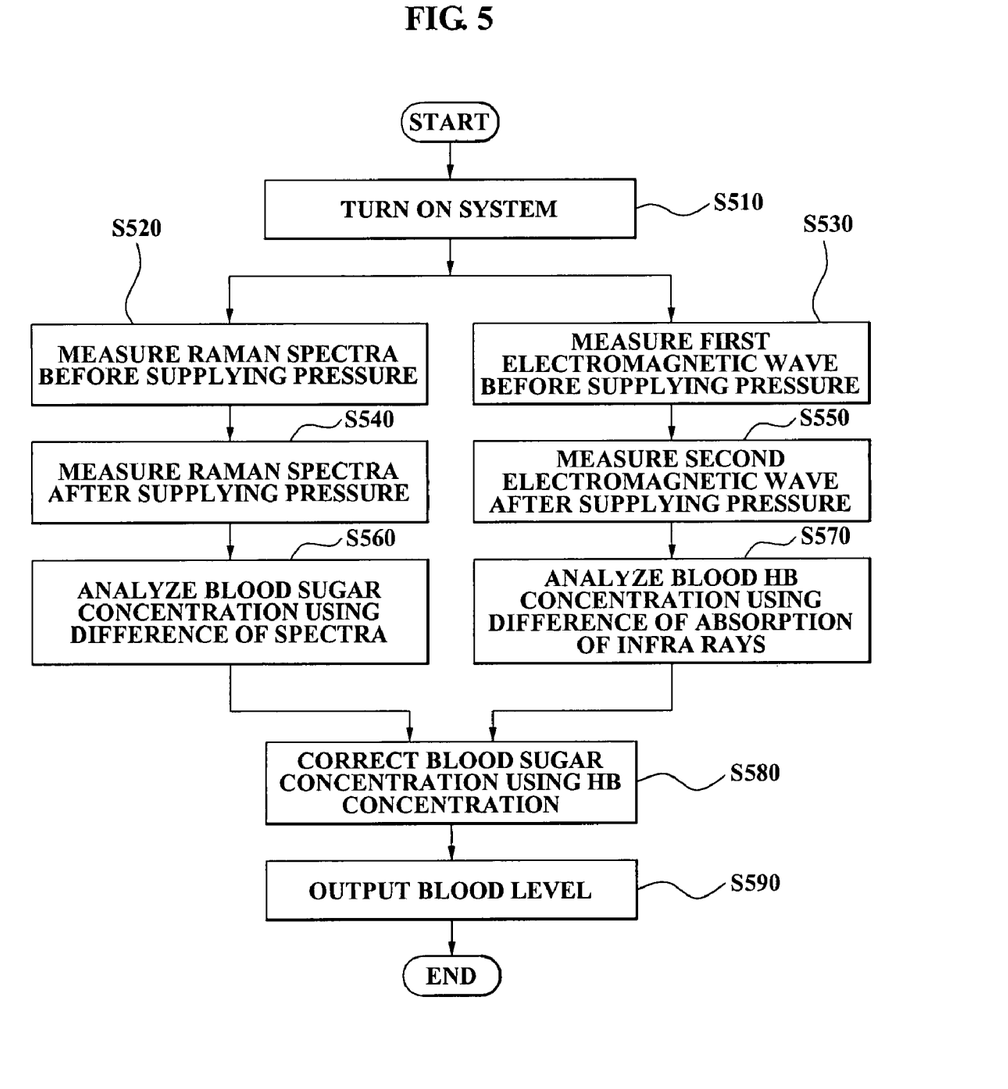
FIG. 5 is a flowchart illustrating operation of the noninvasive in vivo measuring system of FIG. 4.

Hereinafter, operations of the noninvasive in vivo measuring system 300 of FIG. 3 according to an embodiment of the present invention will be described in detail by referring to FIG. 5.

When the noninvasive in vivo measuring system 300 of FIG. 3 according to the embodiment of the present invention is turned on, the tissue modulation unit 310, the R-F measuring unit 320, and the Hb measuring unit 330 start to operate in operation S510.

As illustrated in FIG. 4, before the tissue modulation unit 310 applies the pressure on the predetermined portion of the finger, the R-F measuring unit 320 and the Hb measuring unit 330 respectively measure the Raman spectra and the electromagnetic waves in operations S520 and S530.

The R-F measuring unit 320 generates a laser using the LD 321 in order to obtain the Raman spectra of the laser, which is reflected from the tissue. The laser generated from the LD 321 is collected in the light collector 322 to enter the tissue via a hole on a finger contacting instrument. A predetermined optical system for adjusting a focus of the laser to the light collector 322 may be used. As described, the entered laser is scattered to reflect depending on components in blood. The reflected laser is collected in the light receiver 323 typed in the predetermined optical system, and is transmitted to the spectroscope 324. The spectroscope 324 generates fluorescence spectra by analyzing the laser collected in the light receiver 323. Accordingly, the light sensing array 325 senses the fluorescence spectra, having been analyzed in the spectroscope 324, and converts the sensed analyzed fluorescence spectra into predetermined electrical signals by using a predetermined sensor sensing the finger contacting instrument. The blood sugar analyzer 326 calculates strengths of the fluorescence spectra from the reflected laser and strengths of Raman spectra determined by a glucose component in blood in operation S520. Values calculated by the blood sugar analyzer 326 are stored in a predetermined memory before the tissue modulation unit 310 applies the pressure.

Before applying the pressure, the Hb measuring unit 330 generates predetermined electromagnetic waves using the light source array 331 in order to measure the Hb concentration in another portion of the finger. The light source array 331 includes at least two light sources, and thus, the light source array 331 may include a light source which generates electromagnetic waves having a comparatively greater absorption in the Hb, and may include another light source which generates electromagnetic waves having a comparatively less absorption in the Hb.

The light source array 331 generates the electromagnetic waves having wavelengths of less than approximately 1300 nm. Before the tissue modulation unit 310 applies the pressure, the electromagnetic waves, having been generated from the light source array 331, penetrates the finger to be sensed by the light detector 332. The light detector 332 may be equipped in the finger contacting instrument contacting the finger as illustrated in FIG. 4. The light detector 332 generates the predetermined electrical signal according to the strengths of the electromagnetic waves which have penetrated the finger, subsequently the concentration calculation unit 333 calculates a predetermined value which indicates an amount of absorption of the electromagnetic waves in operation S530. Values calculated by the concentration calculation unit 333 are stored in a predetermined memory before the tissue modulation unit 310 applies the pressure.

After operations S510 and S520, the tissue modulation unit 310 applies the pressure on the tissue, i.e. the predetermined portion of the finger. The pressure sensor 312 of the tissue modulation unit 310 may be equipped in the finger contacting instrument as illustrated in FIG. 4, and senses the pressure between the finger contacting instrument and the tissue. The pressure which is sensed by the pressure sensor is fed back to the pressure apply unit 311, and the pressure apply unit 311 applies the predetermined pressure by increasing or decreasing the sensed pressure to be equal to or less than a predetermined value. The predetermined pressure may be established depending on various conditions such as low blood pressure/high blood pressure, overweight/normal weight, and age.

After the tissue modulation unit 310 applies the pressure, the R-F measuring unit 320 and the Hb measuring unit 330 respectively measure the Raman spectra and the electromagnetic waves in operations S540 and S550, in the same way as operations S520 and S530.

The blood sugar analyzer 326 of the R-F measuring unit 320 measures blood sugar concentration by analyzing the Raman spectra based on a reflection of a laser irradiated on a predetermined portion of the finger before and after applying the pressure on the tissue in operation S560.

Figure 6:
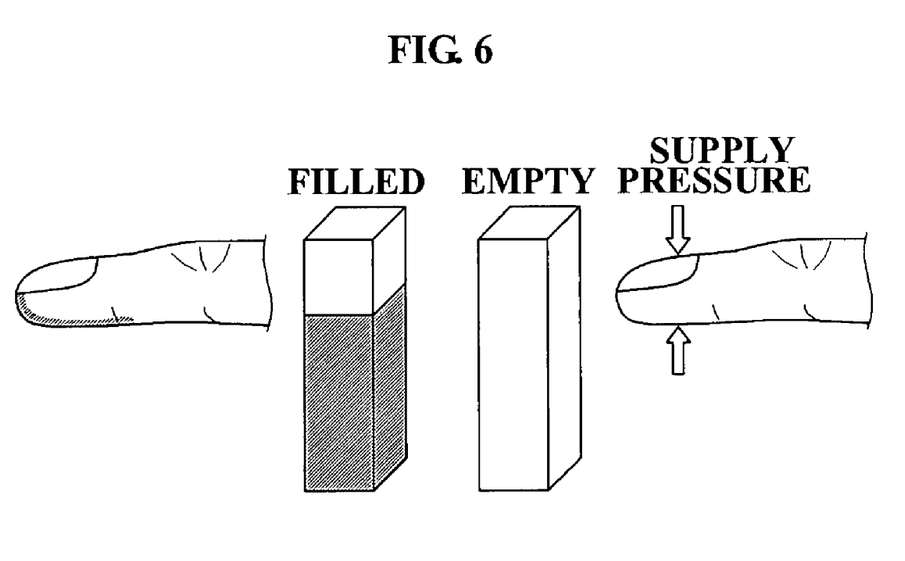
FIG. 6 illustrates a diagram of when blood is eliminated in sample volume when a pressure is applied by a tissue modulation.
Figure 7:
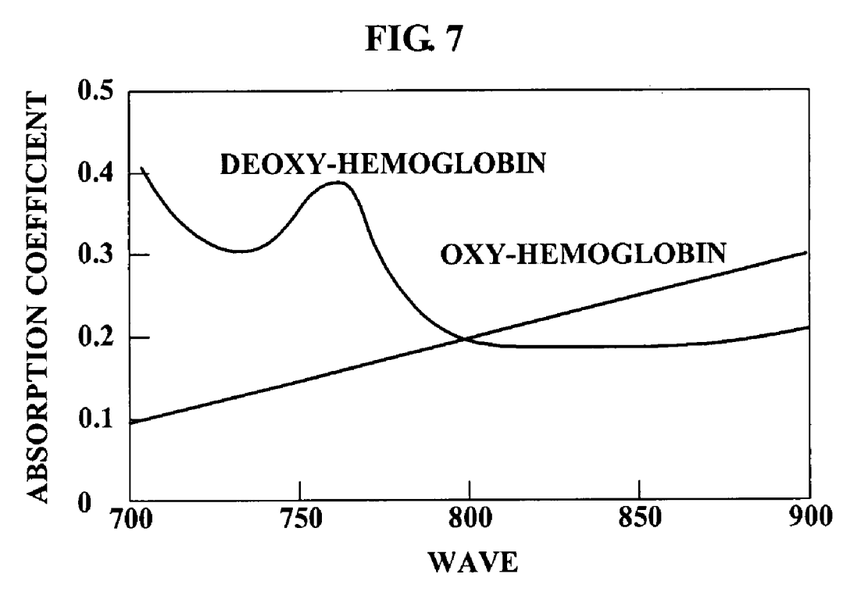
FIG. 7 is a graph illustrating a relation between wavelengths and an Hb absorption coefficient.

As illustrated in FIG. 6, blood is filled under the finger contacting instrument. Components such as H2O, a red blood cell, a white blood cell, an electrolyte, and cholesterol exist in blood, along with glucose and the Hb. When the components in blood are given with the pressure as illustrated in FIG. 6, the components move to another place where the pressure is not given, subsequently the portion of the finger where the pressure is given becomes empty in blood.

As described above, when the tissue modulation unit 310 of FIG. 3 analyzes fluorescence spectra, having been measured by the R-F measuring unit 320 before and after applying the pressure on the finger, strengths of the Raman spectra, which are scattered with the change in blood volume, become different. In an R-F method, a blood sugar level may be measured by analyzing the Raman spectra.

According to the Raman spectrum method, the blood sugar analysis unit 326 of the R-F measuring unit 320 calculates blood sugar concentration based on the strengths of the fluorescence spectra of the reflected laser and the strength of the Raman spectra by the glucose component in blood. A strength of a fluorescence spectrum and a strength of a Raman spectrum when blood volume is empty after applying the pressure on the finger via the tissue modulation unit 310 may be used as reference data. Namely, a difference of the strength of the fluorescence spectra and a difference of the strength of the Raman spectra before and after applying the pressure on the finger by the tissue modulation unit 310 may be used for the calculation of the blood sugar concentration.

The concentration calculation unit 333 of the Hb measuring unit 330 analyzes an amount of absorption of electromagnetic waves in a predetermined portion of the finger, and measures Hb concentration of the tissue before and after applying the pressure on predetermined portion of the finger by the tissue modulation unit 310 in operation S570.

An amount of absorption of electromagnetic waves entering from the light source array to the finger before applying the pressure on the finger is greater than an amount of absorption of electromagnetic waves entering from the light source array to the finger after applying the pressure on the finger since there is much blood in the portion of the finger before applying the pressure on the finger. An Hb absorption coefficient is different depending on each wavelength. The Hb concentration of the finger may be respectively calculated according to an amount of the electromagnetic waves absorbed by blood before and after applying the pressure on the finger by the tissue modulation unit 310 of FIG. 3.

As described above, when the concentration calculation unit 333 of the Hb calculation unit 330 calculates the Hb concentration of the finger, the blood sugar analyzer 326 of the R-F measuring unit 320 calculates a final blood sugar level by correcting the blood sugar concentration measurement, which is measured based on the analysis of the Raman spectra before and after applying the pressure, according to the Hb concentration in operation S580. In this instance, the correcting of the blood sugar concentration may be differently corrected according to the Hb concentration.

FIG. 2 is a graph illustrating a general relation between an Hb level and a blood sugar level.

In FIG. 2, distribution of an Hb concentration measured in the Hb measuring unit 330 of FIG. 3 is illustrated, the distribution displays as the Hb level is less, the blood sugar level becomes increased, conversely the Hb level is greater, the blood sugar level becomes decreased.

Under the circumstance, when a predetermined threshold value, i.e. a normal range of the Hb concentration, corresponds to blood sugar level 150, the blood sugar analyzer 326 of the R-F measuring unit 320 of FIG. 3 decreasingly corrects the measured Hb concentration at a high level, i.e. at a range of less than 12 of FIG. 2, and increasingly corrects the measured Hb concentration at a low level, i.e. at a range of greater than 15 of FIG. 2., consequently the distribution of the Hb concentration becomes close to the threshold value to be paralleled with respect to an entire Hb level.

Accordingly, in the present invention, a blood sugar concentration may be accurately measured since a measured blood sugar concentration is corrected by the Kb concentration and thereby an influence of the Hb is minimized As described above, in the noninvasive in vivo measuring system 300 according to the embodiment of the present invention, a final blood sugar level is outputted after the R-F measuring unit 320 measures the blood sugar concentration based on the Raman spectra before and after applying the pressure on the tissue via the tissue modulation unit 310, and correcting the blood sugar concentration measurement according to the Kb concentration, having been measured by the Hb measuring unit 330.

Figure 8:
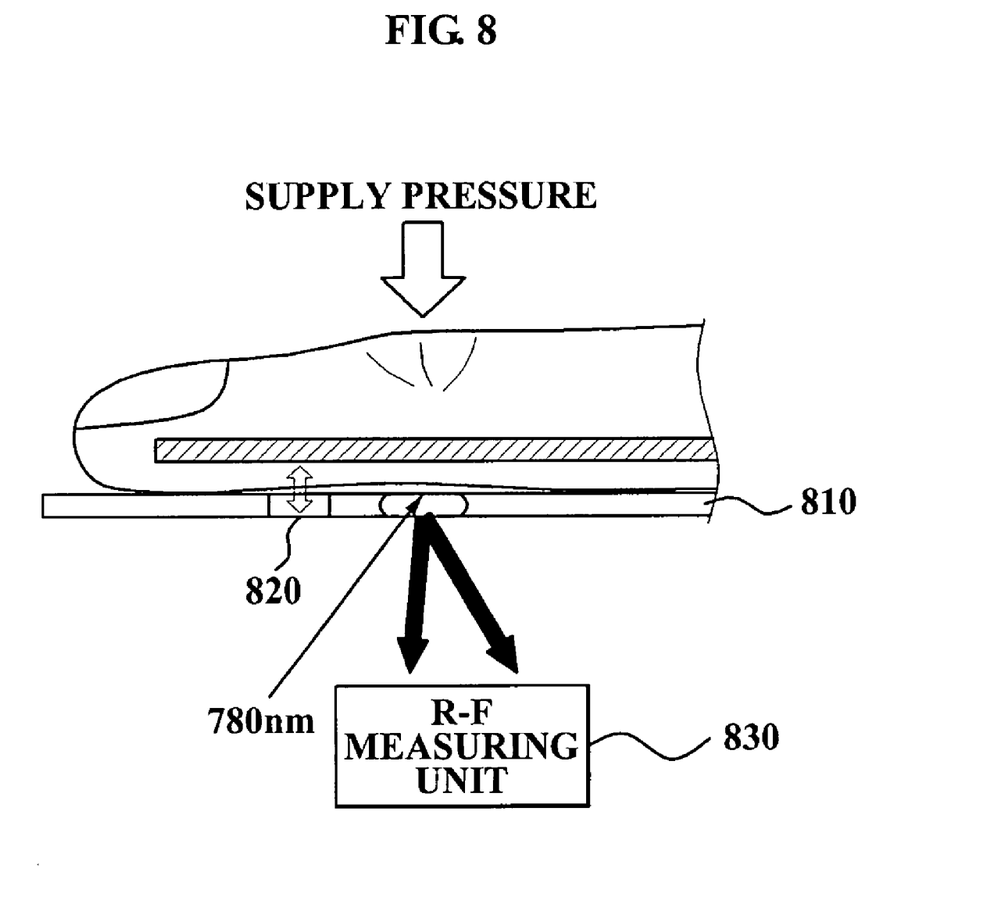
FIG. 8 is a configuration diagram illustrating an entire noninvasive in vivo measuring system which can accurately measure a blood level without correcting a measurement from drawn blood according to another embodiment of the present invention.

FIG. 8 is a configuration diagram illustrating an entire noninvasive in vivo measuring system which can accurately measure a blood level without correcting a measurement from drawn blood according to another embodiment of the present invention.

A pressure sensor 810 is equipped on an inside of a predetermined contact surface, and measures a pressure applied on the contact surface and an external pressure applied on the contact surface. The pressure sensor 810 may be included in a tissue modulation unit in the present invention.

An Hb measuring unit measures Hb concentration before and after applying a pressure, and an R-F measuring unit 830 measures blood sugar concentration before and after applying the pressure.

The Hb measuring unit may include an Hb concentration measuring module 820 inside of the Hb measuring unit, and the Hb concentration measuring module 820 may include at least two light sources by diagonally arranging the at least two light sources around an optical detector in a center of the Hb concentration measuring module 820 and around the optical detector. The Hb concentration measuring module 820 uses a light source having absorption of water less than 1300 nm in order to accurately measure the Hb concentration, and uses a light source having a wavelength of approximately 560 nm to 805 nm.

Particularly, in the embodiment of the specification, the Hb concentration measuring module 820 may be configured in a reflection type, and measures the Hb concentration of the tissue by analyzing information about how the electromagnetic waves of predetermined waves, irradiated on a specific portion of the tissue before and after the applying of the pressure, are reflected. The configuration of the reflection type is to improve measurement accuracy by eliminating an error caused by light preventing obstacles, such as a bone and a large vein, in a finger penetration type.

Also, the Hb concentration measuring unit 820 may improve accuracy when measuring the Hb concentration by analyzing differences of an amount of absorption, which are caused by differences of body fluids in the tissue after applying the pressure on the tissue.

The R-F measuring unit 830 calculates a final blood sugar level by increasingly correcting the blood sugar concentration measurement, having been measured based on an analysis of the Raman spectra, when the Hb concentration is greater than a predetermined threshold value, and calculates the final blood sugar level by decreasingly correcting the blood sugar concentration measurement, having been measured based on the analysis of the Raman spectra, the when the Hb concentration is less than the predetermined threshold value.

Figure 9:
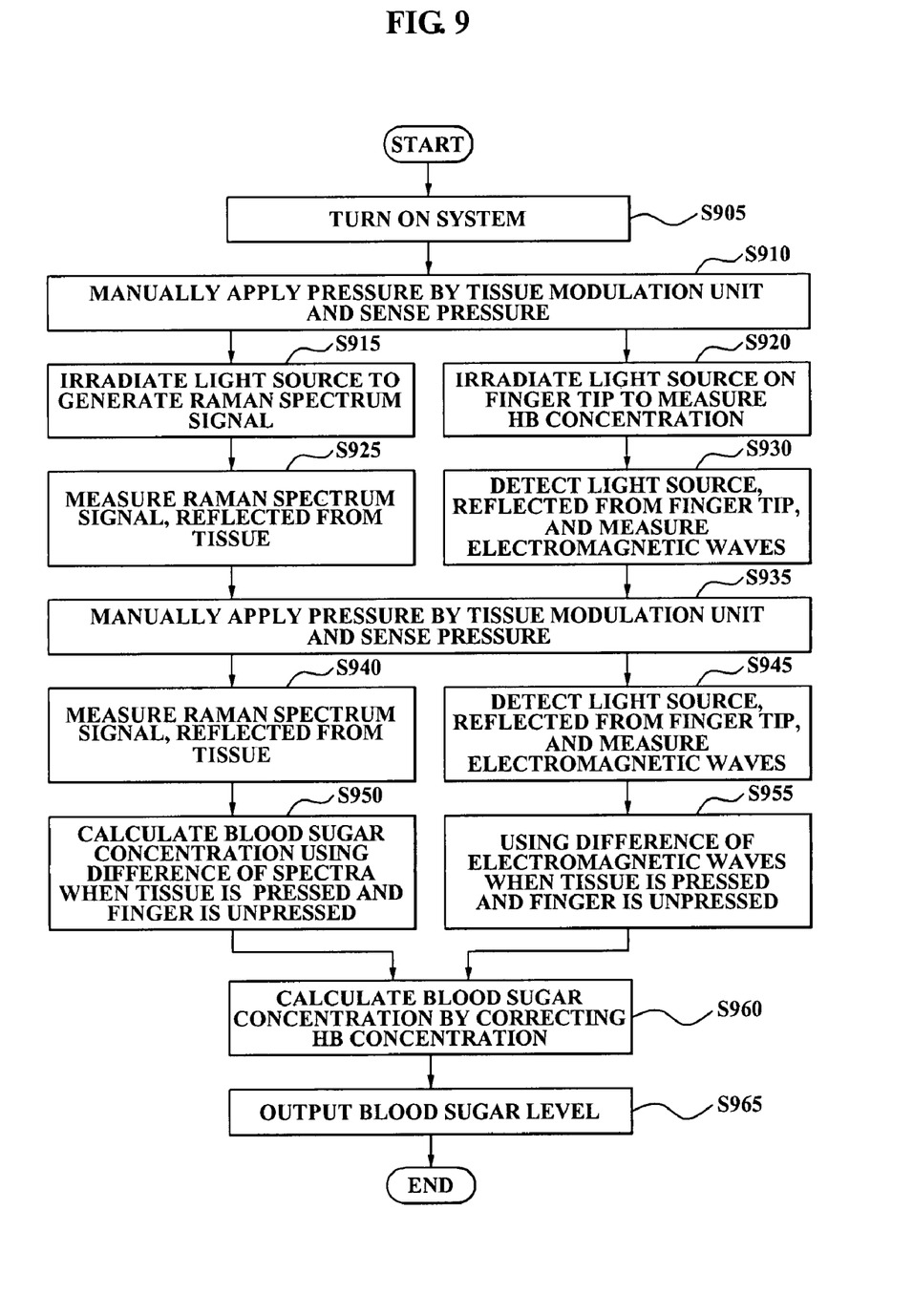
FIG. 9 is a flowchart illustrating operations of the noninvasive in vivo measuring system of FIG. 8.

FIG. 9 is a flowchart illustrating operations of the noninvasive in vivo measuring system of FIG. 8.

In the noninvasive in vivo measuring system according to the present invention operates, a tissue modulation unit including a pressure sensor 810, the R-F measuring unit 830 of FIG. 8, and an Hb measuring unit including an Hb concentration measuring module 820 start to operate when the vivo measuring system according to the present invention is turned on in operation S905.

Before a predetermined portion of a finger is contacted to the tissue modulation unit, i.e. before a pressure is applied from the tissue modulation unit in operation S910, the R-F measuring unit 830 irradiates a light source of approximately 780 nm on the tissue to generate a Raman spectrum signal, and measures a Raman spectrum which is reflected from the tissue in operations S915 and S925.

Also, an Hb concentration measuring module 820 of the Hb measuring unit irradiates at least two light sources, e.g. light sources of 560 nm and 805 nm, on a fingertip, and measures the Hb concentration by detecting electromagnetic waves reflected from the fingertip in operations S920 and S930.

A Raman spectrum signal having been measured by the R-F measuring unit 830 and the Hb concentration having been measured by the Hb concentration measuring module 820 are stored in a predetermined memory.

Later, pressure is manually applied on the finger as a result that the tissue is contacted to the tissue modulation unit in operation S935. A pressure sensor 810 of the tissue modulation unit may be equipped in an inside of a contacting surface as illustrated in FIG. 8, and senses the pressure on the contacting surface.

A result sensed by the pressure sensor 810 is fed back to a pressure apply unit of the tissue modulation unit, and the pressure apply unit applies a predetermined pressure by controlling the sensed result not to be greater than a predetermined value. A strength of the predetermined pressure, which is applied by the pressure apply unit, may be differently determined depending on various conditions such as low blood pressure/high blood pressure, overweight/normal weight, and age.

The R-F measuring unit 830 and the Hb measuring unit measure Raman spectra and the Hb concentration after applying the pressure by replicating operations S925 and S930 in operations S940 and S945.

Subsequently, a blood sugar analyzer of the R-F measuring unit 830 measures blood sugar concentration by analyzing the Raman spectrum before applying the pressure and the Raman spectrum after applying the pressure in operation S950. Namely, the blood sugar analyzer of the R-F measuring unit 830 measures the blood sugar concentration using a fact that strengths of Raman spectra become different at a specific wave.

When fluorescence spectra, having been measured by the R-F measuring unit 830 before and after applying the pressure on the tissue, are analyzed, strengths of Raman spectra become different at a specific wave.

In other words, the blood sugar analyzer of the R-F measuring unit 830 calculates the blood sugar concentration using strength of the fluorescence spectra from the reflection of the laser, and using the strength of the Raman spectra determined by a glucose component in blood. A strength of a fluorescence spectrum and a strength of Raman spectrum when components in blood are removed after applying the pressure on the finger via the tissue modulation unit may be used as reference data.

A concentration calculation unit of the Hb measuring unit analyzes an amount of absorption of electromagnetic waves in a predetermined portion of the finger, i.e. a first portion of the finger, and measures Hb concentration of blood in the tissue before and after applying the pressure on the predetermined portion of the finger by the tissue modulation unit in operation S955.

There is much blood on the first portion before applying the pressure on the finger, conversely, blood is empty on the first portion after applying the pressure on the finger. Accordingly, an amount of reflection of the electromagnetic waves before and after applying the pressure on the first portion of the finger may differ, and the concentration calculation unit of the Hb measuring unit may measure the Hb concentration.

As described above, when the concentration calculation unit of the Hb measuring unit calculates the Hb concentration of the finger, the blood sugar analyzer of the R-F measuring unit 830 calculates to output a final blood level by correcting the blood sugar concentration measurement according to the measured Hb concentration in operations S960 and S965.

In this instance, referring to FIG. 2, the correcting of the blood sugar concentration may be corrected according to the measured Hb concentration As described above, when a measured blood sugar concentration is corrected by the Hb concentration, a blood sugar concentration may be accurately measured since an influence of the Hb is minimized.

Thus, according to the present invention, Hb concentration, i.e. blood sugar concentration, can improve measurement accuracy by eliminating an error caused by light preventing obstacles, such as a bone and a large vein, when measuring the Hb concentration.

The noninvasive in vivo measuring method according to the above-described embodiment of the present invention may be recorded in computer-readable media including program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM disks and DVD; magneto-optical media such as optical disks; and hardware devices that are specially configured to store and perform program instructions, such as read-only memory (ROM), random access memory (RAM), flash memory, and the like. The media may also be a transmission medium such as optical or metallic lines, wave guides, and the like, including a carrier wave transmitting signals specifying the program instructions, data structures, and the like. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention.

As described above, the noninvasive in vivo measuring system and the noninvasive in vivo measuring method may more accurately measure blood sugar concentration since other components in blood are eliminated, particularly components which affects the blood sugar concentration whose Hb concentration is measured in an R-F method, is eliminated.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. A noninvasive in vivo measuring system comprising:
    a tissue modulation unit configured to apply a pressure on a tissue;
    a hemoglobin (Hb) measuring unit configured to analyze an amount of absorption of electromagnetic waves on a first portion of the tissue before and after the application of the pressure by the tissue modulation unit, and configured to measure a Hb concentration of the tissue; and
    a Raman-fluorescence (R-F) measuring unit configured to measure a blood sugar concentration by analyzing Raman spectra based on a reflection of a laser irradiated on a second portion of the tissue before and after the application of the pressure by the tissue modulation unit, and configured to calculate a final blood sugar level by correcting the blood sugar concentration measurement, based on the measured Hb concentration,
    wherein the R-F measuring unit is configured to calculate the final blood sugar level by increasingly correcting the blood sugar concentration measurement, having been measured based on the Raman spectra, when the Hb concentration is greater than a predetermined threshold value, and is configured to calculate the final blood sugar level by decreasingly correcting the blood sugar concentration measurement, having been measured based on the Raman spectra, when the Hb concentration is less than the predetermined threshold value.

2. The system of claim 1, wherein the Hb measuring unit is configured to calculate the Hb concentration of the tissue by analyzing absorption of predetermined electromagnetic waves before and after the application of the pressure on the tissue.

3. The system of claim 2, wherein wavelengths of the electromagnetic waves before and after the application of the pressure on the tissue are less than approximately 1300 nm.

4. The system of claim 1, wherein the Hb measuring unit comprises:
    a light source array, having at least two light sources, to generate the electromagnetic waves;
    a light detector configured to sense electromagnetic waves after penetration of the first portion of the tissue by the electromagnetic waves; and
    a concentration calculator configured to calculate the Hb concentration using a difference of the absorption of electromagnetic waves, having been sensed by the light detector.

5. The system of claim 4, wherein the light detector is equipped in an instrument for contacting the tissue.

6. The system of claim 5, wherein the tissue modulation unit is configured to apply a predetermined pressure between the instrument for contacting the tissue and a portion of the tissue.

7. The system of claim 5, wherein the tissue modulation unit comprises:
    a pressure sensor configured to sense the pressure applied on the portion of the tissue, and configured to be equipped in the instrument for contacting the tissue; and
    a pressure applier configured to apply at least a single type of the pressure between the instrument for contacting the tissue and the portion of the tissue by using a result of the sensing, which is fed back from the pressure sensor.

8. The system of claim 1, wherein the R-F measuring unit is configured to calculate the blood sugar concentration by using strengths of fluorescence spectra from the reflection of the laser, and strengths of Raman spectra determined by a glucose component in blood.

9. The system of claim 1, wherein the tissue corresponds to a portion of a finger.

10. A noninvasive in vivo measuring system comprising:
    a tissue modulation unit configured to apply a pressure on a tissue;
    a Hb measuring unit configured to analyze an amount of reflection of electromagnetic waves, having been irradiated on a first portion of a tissue, before and after the application of pressure by the tissue modulation unit, and measuring Hb concentration of the tissue; and an R-F measuring unit configured to measure Hb concentration of the tissue by analyzing Raman spectra of reflection of lasers, having been irradiated on a second portion of the tissue, before and after the application of pressure by the tissue modulation unit, and configured to calculate a final blood sugar level by increasingly or decreasingly correcting blood sugar concentration measurement according to the measured Hb concentration, wherein the Hb measuring unit is configured to identify differences of body fluids in a first portion of the tissue before and after the application of the pressure on the tissue using the reflection of the electromagnetic waves, and is configured to measure the Hb concentration by analyzing differences of absorption with respect to the identified differences of body fluids in the first portion of the tissue.

11. A noninvasive in vivo measuring method comprising:
analyzing an amount of absorption of electromagnetic waves on a first portion of a tissue;
analyzing Raman spectra based on a reflection of a laser irradiated on a second portion of the tissue;
using a tissue modulation unit to apply a pressure on the tissue;
using a hemoglobin (Hb) measuring unit to analyze the amount of absorption of electromagnetic waves on the first portion of the tissue after the applying of the pressure;
using a Raman-fluorescence (R-F) measuring unit to analyze the Raman spectra based on the reflection of the laser irradiated on the second portion of the tissue after the applying of the pressure;
measuring Hb concentration of the tissue using a difference of the absorption of the electromagnetic waves on the first portion of the tissue before and after applying the pressure;
measuring blood sugar concentration of the tissue using a difference of the Raman spectra on the second portion of the tissue before and after the applying of the pressure; and
measuring a final blood sugar level by correcting the blood sugar concentration measurement according to the measured Hb concentration.

12. The method of claim 11, wherein at least two waves, having different absorption rates of the Hb, are used for the electromagnetic waves.

13. The method of claim 12, wherein wavelengths of the electromagnetic waves are less than approximately 1300 nm.

14. The method of claim 11, wherein the final blood sugar level is calculated by increasingly correcting the blood sugar concentration measurement, having been measured based on the Raman spectra, when the Hb concentration is greater than a predetermined threshold value, and wherein the final blood sugar level is calculated by decreasingly correcting the blood sugar concentration measurement, having been measured based on the Raman spectra, when the Hb concentration is less than the predetermined threshold value.

15. The method of claim 11, wherein the blood sugar concentration is calculated using a strength of fluorescence spectra from the reflection of the laser, and using a strength of Raman spectra determined by a glucose component in blood.

16. The method of claim 11, wherein at least one predetermined pressure is applied between an instrument for contacting the tissue and a portion of the tissue.

17. A noninvasive in vivo measuring method comprising:
analyzing an amount of reflection of electromagnetic waves on a first portion of a tissue;
analyzing Raman spectra using reflection of lasers, having been irradiated on a second portion of the tissue;
using a tissue modulation unit to apply a pressure on the tissue;
using a hemoglobin (Hb) measuring unit to analyze an amount of reflection of electromagnetic waves on the first portion of the tissue before and after the applying of the pressure;
using a Raman-fluorescence (R-F) measuring unit to analyze Raman spectra using reflection of lasers, having been irradiated on the second portion of the tissue before and after the applying of the pressure;
measuring Hb concentration of the tissue using a difference of the amount of reflection of electromagnetic waves on the first portion of the tissue before and after the applying of the pressure;
measuring blood sugar concentration of the tissue using a difference of the Raman spectra before and after the applying of the pressure; and
calculating a final blood sugar level by increasingly or decreasingly correcting the measured blood sugar concentration according to the measured Hb concentration.

18. A non-transitory computer-readable storage medium storing a program for implementing a noninvasive in vivo measuring method, the method comprising:
analyzing an amount of absorption of electromagnetic waves on a first portion of a tissue;
analyzing Raman spectra based on a reflection of a laser irradiated on a second portion of the tissue;
applying a pressure on the tissue;
analyzing the amount of absorption of electromagnetic waves on the first portion of the tissue after the applying of the pressure;
analyzing the Raman spectra based on the reflection of the laser irradiated on the second portion of the tissue after the applying of the pressure;
measuring Hb concentration of the tissue using a difference of the absorption of the electromagnetic waves on the first portion of the tissue before and after applying the pressure;
measuring blood sugar concentration of the tissue using a difference of the Raman spectra on the second portion of the tissue before and after the applying of the pressure; and measuring a final blood sugar level by correcting the blood sugar concentration measurement according to the measured Hb concentration.

* * * * *